United States Patent [19]

Shepard

[11] Patent Number: 4,542,152

[45] Date of Patent: Sep. 17, 1985

[54] 5-[PHENYLSULFONYL(OR SULFINYL)]THIOPHENE-2-SULFONAMIDES FOR THE TOPICAL TREATMENT OF ELEVATED INTRAOCULAR PRESSURE

[75] Inventor: Kenneth L. Shepard, North Wales, Pa.

[73] Assignee: Merck & Co., Inc., Rahway, N.J.

[21] Appl. No.: 505,673

[22] Filed: Jun. 20, 1983

Related U.S. Application Data

[63] Continuation-in-part of Ser. No. 497,388, May 23, 1983, abandoned.

[51] Int. Cl.$^4$ .............................................. A61K 31/38
[52] U.S. Cl. ..................................... 514/445; 514/913
[58] Field of Search .......................................... 424/275

[56] References Cited

U.S. PATENT DOCUMENTS 4,029,809 6/1977 Smith et al. ........................ 424/275
4,386,098 5/1983 Woltersdorf et al. .............. 424/270

FOREIGN PATENT DOCUMENTS 0036351 9/1981 European Pat. Off. .
1459571 12/1976 United Kingdom .

OTHER PUBLICATIONS

Gelatt et al.–Am. J. Vet. Res. 40(3)–334–345 (1979), "Ocular Hypotensive Effects of Carbonic Anhydrase Inhibitors in Normotensive and Glaucomatous Beagles".

*Primary Examiner*—Douglas W. Robinson
*Attorney, Agent, or Firm*—William H. Nicholson; Mario A. Monaco

[57] ABSTRACT

5-[Phenylsulfonyl(or sulfinyl)]thiophene-2-sulfonamides are useful for the topical treatment of elevated intraocular pressure. Ophthalmic compositions including drops and inserts are disclosed.

9 Claims, No Drawings

5-[PHENYLSULFONYL(OR SULFINYL)]THIOPHENE-2-SULFONAMIDES FOR THE TOPICAL TREATMENT OF ELEVATED INTRAOCULAR PRESSURE

SUMMARY OF THE INVENTION

This is a continuation-in-part of a co-pending application Ser. No. 497,388 filed May 23, 1983 now abandoned.

This invention relates to 5-[phenylsulfonyl(or sulfinyl)]thiophene-2-sulfonamides, found to be useful in the reduction of elevated intraocular pressure. More particularly this invention relates to compositions including the compound of the structural formula:

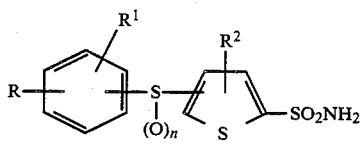

as well as the ophthalmologically acceptable salts thereof wherein the active entity is incorporated in an ophthalmologically suitable carrier therefor. This invention especially relates to methods for the treatment of elevated intraocular pressure, especially when accompanied by pathological damage such as in the disease known as glaucoma.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure.

Although pilocarpine and physostigmine increase the outflow of aqueous humor and thus reduce intraocular pressure, they have no effect on the biological mechanism largely responsible for aqueous humor formation, the carbonic anhydrase pathway. Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of exposing body carbonic anhydrase to their action. Such a potential gross disruption of a basic enzyme system is justified only during an acute attack of alarmingly elevated intraocular pressure, or when no other agent is effective. Despite the desireability of directing the carbonic anhydrase inhibitor only to the desired ocular target tissue, no topically effective carbonic anhydrase inhibitors are presently available for clinical use.

DESCRIPTION OF THE INVENTION

Compositions of 5-[phenylsulfonyl(or sulfinyl)]thiophene-2-sulfonamides or ophthalmologically acceptable salts thereof are now found to inhibit carbonic anhydrase and, moreover, to lower intraocular pressure when topically administered to the mammalian eye, particularly in the form of drops or inserts. Examples of such ophthalmologically acceptable salts include the alkali metal salts.

A number of 5-[phenylsulfonyl(or sulfinyl)]thiophene-2-sulfonamides have been described in British Patent No. 1,459,571 and *J. Med. Chem.*, 24, 959 (1981). Those that are active in the novel compositions of this invention have structural formula:

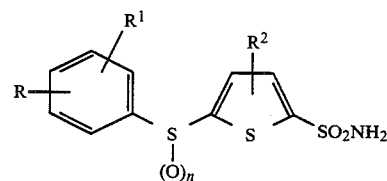

or an ophthalmologically acceptable salt thereof, wherein:

n is 1 or 2;

R is (1) —OH (2)

wherein $R^3$ and $R^4$ are independently selected from:
(a) hydrogen,
(b) $C_{1-3}$alkyl,
(c) $C_{2-5}$alkanoyl,
(d) $C_{3-6}$cycloalkylcarbonyl,
(e) benzoyl,
(f) $C_{1-3}$alkoxycarbonyl,
(g) N-$C_{1-3}$alkyl carbamoyl,
(h) $C_{1-3}$alkylsulfonyl, (3)

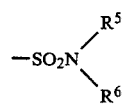

wherein $R^5$ and $R^6$ are independently selected from hydrogen, $C_{1-3}$alkyl or $C_{3-6}$cycloalkyl, (4) —$CH_2CO_2H$, (5)

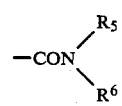

(6) —$CO_2H$, or (7)

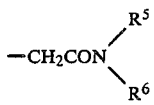

R¹ is
(1) hydrogen,
(2) halo, such as chloro, bromo or fluoro,
(3) C₁₋₃alkyl or
(4) C₁₋₃alkoxy; and R² is
(1) hydrogen, or
(2) halo, such as chloro or bromo.

A preferred embodiment of the compounds active in the novel compositions of this invention includes those compounds wherein:
n is 2;
R is
(1) —OH,
(2)

wherein R³ and R⁴ are independently selected from:
(a) hydrogen,
(b) C₂₋₅alkanoyl,
(c) C₁₋₃alkoxysulfonyl,
(d) C₁₋₃alkoxycarbonyl,
(e) N-C₁₋₃alkylcarbamoyl,
(f) C₃₋₆cycloalkylcarbonyl,
and R¹ and R² are both hydrogen.

Representative species are those defined by the following table wherein n is 1 or 2:

| R | R¹ | R² |
|---|----|----|
| (1) 4-NHCOCH₃ | H | H |
| (2) 4-NHCOC₆H₅ | H | H |
| (3) 4-SO₂NH₂ | H | H |
| (4) 4-NHCOC₂H₅ | H | H |
| (5) 4 NHCOCH₃ | 2-Cl, 5-CH₃ | H |
| (6) 4-NHSO₂CH₃ | H | H |
| (7) 4-NHCOOCH₃ | H | H |
| (8) 3-NHCOCH₃ | 4-OCH₃ | H |
| (9) 4-CH₂COOH | H | H |
| (10) 4-CH₂CONHCH₃ | H | H |
| (11) 4-NHCONHCH₃ | H | H |
| (12) 4-NHCOCH₃ | 3-Cl | H |
| (13) 4-NHCOCH₃ | H | 4-Br |
| (14) 4-NHCOCH₃ | H | 3-Cl |
| (15) 4-NHCOCH(CH₃)₂ | H | H |
| (16) 4-NHCOCH₂CH₂CH₃ | H | H |
| (17) 4-NHCOC(CH₃)₃ | H | H |
| (18) 4-NHCOCH₃ | H | 4-Cl |
| (19) 4-NHCOCH₃ | H | 3-Br |
| (20) 3-NHCOOC₂H₅ | H | H |
| (21) 4-NHCO—▷ | H | H |
| (22) 4-CONH₂ | H | H |
| (23) 3-CO₂H | H | H |
| (24) 3-CONH₂ | H | H |
| (25) 3-CONHCH₃ | H | H |
| (26) 3-CONHCH(CH₃)₂ | H | H |
| (27) 4-CH₂CONH₂ | H | H |
| (28) 2-CONH₂ | H | H |
| (29) 3-NHCOCH₃ | H | H |
| (30) 4-OH | H | H |
| (31) 4-CH₂CONHC(CH₃)₃ | H | H |
| (32) 3-CONH—⬠ | H | H |

The most preferred species is 5-[(4-hydroxyphenyl)-sulfonyl]thiophene-2-sulfonamide.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. Generally, the drug is present in such vehicles in an amount of from 0.1 to about 25% by weight or more. Preferably the drug is present in an amount of from 0.1 to 15% by weight, and most preferably from 0.25 to 5% by weight.

While many patients find liquid medication to be entirely satisfactory, others may prefer a solid medicament that is topically applied to the eye, for example, a solid dosage form that is suitable for insertion into the cul-de-sac. To this end the carbonic anhydrase inhibiting agent can be included with a non-bioerodible insert, i.e. one which after dispensing the drug remains essentially intact, or a bioerodible insert, i.e. one that either is soluble in lacrimal fluids, or otherwise disintegrates. While the insert employed is not critical, those disclosed in U.S. Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, the insert described below is found preferable.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert, is available in several polymeric forms, all of which are suitable in the preparation of these inserts. Thus, the product sold by Hercules, Inc. of Wilmington, Del., under the name KLUCEL such as KLUCEL HF, HWF, MF, GF, JF, LF and EF which are intended for food or pharmaceutical use, are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX, a polymer supplied by Union Carbide Co., may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and, accordingly, the medicament in any desired length of time. The inserts, therefore, can be prepared to allow for retention and, accordingly, effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be prepared readily, for example, by dissolving the medicament and the polymer in a suitable solvent and the solution evaporated to afford a thin film of the medicated polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size which readily fits into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5–20 mm. or ovals of comparable size. Similarly, extruded rods having a diameter between about 0.5 and 1.5 mm. can be cut into suitable sections to provide the desired amount of medicated polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the terms smooth and sharp edges or corners are subjective terms, in this application these terms are used to indicate that excessive irritation of the eye will not result from the use of the inert.

The medicated ocular inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from 0% up to about 30% by weight. A particularly preferred plasticizer is water which is present in amounts of at least about 5% up to 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7–8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 35% by weight of insert, but preferably not more than 25% by weight.

The following examples of ophthalmic formulations are given by way of illustration.

EXAMPLE 1

| Solution Composition | a | b |
| --- | --- | --- |
| 5-[(4-Hydroxyphenyl)sulfonyl]-thiophene-2-sulfonamide | 1 mg. | 15 mg. |
| Monobasic sodium phosphate .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and admixed with water. The pH of the resulting admixture is adjusted to 6.8 and the final formulation diluted to volume. The formulation is rendered sterile by appropriate means, such as starting the preparative procedure with sterile components and proceeding under sterile conditions, irradiating or autoclaving the finished formulation, or the like.

EXAMPLE 2

5-[(4-Hydroxyphenyl)sulfonyl]thiophene-2-sulfonamide: 5 mg.
petrolatum q.s. ad.: 1 gram Compound I and the petrolatum are aseptically combined.

EXAMPLE 3

5-[(4-Hydroxyphenyl)sulfonyl]thiophene-2-sulfonamide: 1 mg
Hydroxypropylcellulose q.s.: 12 mg.

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 4

5-[(4-Hydroxyphenyl)sulfonyl]thiophene-2-sulfonamide: 1 mg.
Hydroxypropyl cellulose q.s. ad.: 12 mg.

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 5

5-[(4-Hydroxyphenyl)sulfonyl]thiophene-2-sulfonamide: 1 mg.
Hydroxypropylmethyl cellulose q.s. ad.: 12 mg.

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 6

5-[(4-Hydroxyphenyl)sulfonyl]thiophene-2-sulfonamide: 1 mg.
Hydroxypropylmethyl cellulose q.s. ad.: 12 mg.

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° 1 C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

After packaging a convenient quantity of inserts, usually a single dose, the package is exposed to a sterilizing quantity of radiation. The preferred packaging employs sealing the inserts between layers of film or foil and then sealing or laminating the layers together about the edges. The techniques for performing the sterilization are well known and accepted, for example, as outlined in International Atomic Energy Commission, *Code of Practice for Radiosterilization of Medical Products*, 1967, pp. 423–431; and Block, *Disinfection, Sterilization and Preservation*, 2nd Ed., Lea & Febiger, Philadelphia, 1977, pp. 542–561.

The required quantity of irradiation can be determined experimentally by testing irradiated inserts for viable bacteria. Generally, the amount of irradiation desired to achieve sterilization is defined by the $D_{10}$ value. The $D_{10}$ value is the radiation dose that will reduce a given population of organisms by a factor of 10. Based on $D_{10}$ values, experimentally obtained for *Bacillus pumilus*, and presterilization contamination levels, a dose of 1.36 megarads is effective in obtaining a sterile product.

Similarly the other formulations can be rendered sterile or pathogen-free by irradiation or other means well known in the art.

The drops, heretofore described in Example 1, are used in the usual way employing one to two drops per eye per patient per day. When inserts are employed usually one insert per patient per eye per day is satisfactory. Elevated intraocular pressure is a condition that must be carefully monitored on an individual basis. Thus an intraocular pressure lowering amount can be as little as 0.001–0.01 mg to as much as 0.100–0.250 mg per eye per patient per day of active medicament. As the individual differences between patient drug response are encountered and as experience with the medicament increases and information accumulates because of a larger patient population being developed, the daily ocular dose for the median population group can be stated with greater statistical accuracy. It may well be found that only a few patients respond to the minimal dose, and then only for a transient period. Also only a few patients may require administration of the drug at the higher dosage ranges. The dose also may be divided for administration. Thus, the quantities set forth previously can be administered in a course of individual deliveries comprising 1–4 or more times per day.

The concentration of active drug in any formulation can vary within a wide range. Clearly, as a function of concentration, the desired dose of formulation will consequently vary for example from a single drop or insert or multiple drops or inserts or larger or smaller inserts.

Although the thrust of this invention is to obtain a composition and method for topical delivery to the eye, it should be appreciated that the 5-[phenylsulfonyl(or sulfinyl)]-thiophene-2-sulfonamides can also be administered systemically by classical routes for carbonic anhydrase inhibitors. These routes include oral and intravenous, although other routes can be employed. The 5-[phenylsulfonyl(or sulfinyl)]thiophene-2-sulfonamide or salts thereof can be used in a manner analagous in dosage and formulation to ethoxzolamide. Therefore in acute attacks, or where otherwise indicated the suitable route may be other than topical. Yet, for routine administration, the preferred route is of course by means of topical delivery.

What is claimed is:

1. An ophthalmic composition for the topical treatment of glaucoma and ocular hypertension comprising a solid water soluble polymer and from 0.1 to 35% by weight of the carbonic anhydrase inhibitor 5-[(4-hydroxyphenyl)sulfonyl]thiophene-2-sulfonamide.

2. The composition of claim 1 which comprises from 0.25 to 5% by weight of the carbonic anhydrase inhibitor.

3. The composition of claim 1 wherein the solid polymer is hydroxypropyl cellulose or polyvinyl alcohol.

4. A method for treating elevated intraocular pressure which comprises topically applying to an eye in need of such treatment, an effective intraocular pressure lowering amount of the carbonic anhydrase inhibitor, 5-[(4-hydroxyphenyl)sulfonyl]thiophene-2-sulfonamide.

5. The method according to claim 4 wherein the carbonic anhydrase inhibitor is administered in a polymeric insert.

6. The method according to claim 5 where said insert comprises from 0.01 to 35% by weight of the carbonic anhydrase inhibitor.

7. The method according to claim 5 wherein the polymer is hydroxypropylcellulose or polyvinyl alcohol.

8. The method according to claim 4 wherein the carbonic anhydrase inhibitor is administered in an ointment base.

9. The method according to claim 4 wherein the carbonic anhydrase inhibitor is administered in a liquid vehicle.

* * * * *